(12) United States Patent
Han et al.

(10) Patent No.: US 7,896,811 B2
(45) Date of Patent: Mar. 1, 2011

(54) PORTABLE DEVICE HAVING BIOSIGNAL-MEASURING INSTRUMENT

(75) Inventors: Wan Taek Han, Hwaseong-si (KR); Jin Sang Hwang, Yongin-si (KR); Sang Hoon Shin, Seongnam-si (KR); Hyung Sok Yeo, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 437 days.

(21) Appl. No.: 11/432,546

(22) Filed: May 12, 2006

(65) Prior Publication Data
US 2007/0021676 A1 Jan. 25, 2007

(30) Foreign Application Priority Data
Jul. 21, 2005 (KR) ...................... 10-2005-0066162

(51) Int. Cl.
A61B 5/02 (2006.01)
(52) U.S. Cl. .......................... 600/500; 600/481; 600/509
(58) Field of Classification Search ................. 600/481, 600/500–525
See application file for complete search history.

(56) References Cited

U.S. PATENT DOCUMENTS

| | | | | | |
|---|---|---|---|---|---|
| 5,191,891 | A | * | 3/1993 | Righter ........................ | 600/523 |
| 5,316,008 | A | * | 5/1994 | Suga et al. .................. | 600/513 |
| 5,467,768 | A | * | 11/1995 | Suda et al. .................. | 600/391 |
| 5,613,495 | A | * | 3/1997 | Mills et al. .................. | 600/509 |
| 6,754,517 | B2 | * | 6/2004 | Nissila ........................ | 600/384 |
| 7,171,259 | B2 | * | 1/2007 | Rytky .......................... | 600/509 |
| 2001/0003792 | A1 | * | 6/2001 | Ogura et al. ................. | 600/500 |
| 2004/0106872 | A1 | * | 6/2004 | Kosuda ........................ | 600/485 |
| 2005/0116820 | A1 | * | 6/2005 | Goldreich .............. | 340/539.12 |
| 2005/0251059 | A1 | * | 11/2005 | Kim ............................ | 600/513 |
| 2006/0009698 | A1 | * | 1/2006 | Banet et al. .................. | 600/485 |
| 2006/0258944 | A1 | * | 11/2006 | Takahashi et al. ........... | 600/485 |
| 2007/0100247 | A1 | * | 5/2007 | Platt et al. .................... | 600/513 |
| 2008/0228089 | A1 | * | 9/2008 | Cho et al. .................... | 600/485 |

FOREIGN PATENT DOCUMENTS

JP    7-16215    1/1995

(Continued)

*Primary Examiner* — Charles A Marmor, II
*Assistant Examiner* — Karen E Toth
(74) *Attorney, Agent, or Firm* — Staas & Halsey LLP

(57) ABSTRACT

A portable device having a biosignal measuring instrument includes: at least one first electrocardiogram signal sensor portion on a first surface of the portable device that contacts a first hand of a user, to measure a first electrocardiogram signal of the user; at least one second electrocardiogram signal sensor portion on a second surface of the portable device that contacts a wrist of a second hand of the user, to measure a second electrocardiogram signal from the wrist; a pulse waveform sensor on the second surface and in parallel with the second electrocardiogram signal sensor portion, to sense a pulse waveform from the wrist; a waveform controller generating an electrocardiogram waveform of the user from the measured first electrocardiogram signal and second electrocardiogram signal, generating a pulse waveform of the user from the sensed pulse waveform, and detecting at least one characteristic point of the pulse waveform by referring to the electrocardiogram waveform; and an output portion providing a result of the pulse wave analysis based on the at least one detected characteristic point of the user.

4 Claims, 7 Drawing Sheets

FOREIGN PATENT DOCUMENTS

| | | |
|---|---|---|
| JP | 7-31593 | 2/1995 |
| JP | 11-047107 | 2/1999 |
| JP | 2003-144392 | 5/2003 |
| KR | JP 05-176902 | 7/1993 |
| KR | 2001-0106960 | 12/2001 |
| KR | 2003-0074520 | 9/2003 |
| KR | 10-2004-0020584 | 3/2004 |
| KR | 10-2004-0032451 | 4/2004 |
| KR | 10-2005-0008972 | 1/2005 |

\* cited by examiner (a)

(b)

PORTABLE DEVICE HAVING BIOSIGNAL-MEASURING INSTRUMENT

CROSS-REFERENCE TO RELATED APPLICATION

This application claims the benefit of Korean Patent Application No. 10-2005-0066162, filed on Jul. 21, 2005, in the Korean Intellectual Property Office, the disclosure of which is incorporated herein by reference.

BACKGROUND OF THE INVENTION

1. Field of the Invention

The present invention relates to a portable device having a biosignal measuring instrument, and more particularly, to a portable device having a biosignal measuring instrument which can measure a user's electrocardiogram signal and pulse waveform by providing an electrocardiogram signal sensor and a pulse sensor at predetermined positions of the portable device, respectively, such that the user may measure his/her electrocardiogram signal and pulse waveform simultaneously by himself/herself, and detect the user's biosignal more accurately by detecting at least one characteristic point of the pulse waveform with reference to the electrocardiogram waveform.

2. Description of Related Art

As used in the present specification, the term "Ubiquitous" means an information communication environment where a user can be free to access networks at any place without being conscious of the surrounding networks or computers. If ubiquitous is commercialized, anyone can readily use information technology not only at home or in a car, but also even on a mountaintop. Also, the commercialization of Ubiquitous may expand the information technology industry or the scope corresponding thereto by increasing the number of computer users who are connected to networks. Because of its advantage that users can access networks without restriction to time and place, not to mention its portability and convenience, countries worldwide are expanding development and competing in Ubiquitous-related technology now.

Ubiquitous-related technology may be applied to myriad field in human life. In particular, Ubiquitous-HealthCare (hereinafter, U-HealthCare) has recently been in the spotlight as a notable technology area due to the "well-being" boom. U-HealthCare means Ubiquitous technology which enables anyone to readily receive medical services at any time and at any place by installing medical service-related chips or sensors in places of the user's living space. With U-HealthCare, various types of medical attention, such as physical examinations, disease management, emergency care, consultation with a doctor and the like, which currently are only performed in hospitals, may be naturally integrated into our daily lives, thus may be accomplished without going to a hospital.

For example, a diabetic may wear a belt having a blood-sugar management system for blood-sugar management. A blood-sugar sensor attached to the belt may check the blood-sugar of the diabetic upon a specified occasion, and calculate the amount of required insulin corresponding thereto. When the blood-sugar of the diabetic becomes drastically low or high, the belt may provide the blood-sugar information to his/her attending physician via a wireless network, and the attending physician who has received the blood-sugar information may write out an optimal prescription or take the optimal action for the medical emergency.

As an example of U-HealthCare, a portable device is currently being developed and used which can measure an electrocardiogram signal, body fat, or other sorts of biosignals such as a pulse waveform.

Korean Patent Publication No. 10-2004-0020584 entitled "Automatic Blood Pressure Measuring Apparatus and Method" discloses the configuration of receiving a pulse waveform and an electrocardiogram signal from a pressure sensor and an electrocardiogram signal measuring instrument, analyzing the correlation between both said signals, calculating the systolic and diastolic pressure on the basis of the analyzed data, and displaying the same. However, the automatic blood pressure measuring instrument according to this publication includes a pulse waveform sensor measuring pulse waveforms and an electrocardiogram signal sensor measuring electrocardiogram signals as separate units, not as an integrated unit. Thus, it is inconvenient for a user to carry and also, there is an inconvenience the user must bear in that the current electrocardiogram signal sensor must attach its electrodes to the user's own arm and leg.

Also, Korean Patent Publication No. 10-2005-008972 entitled "Portable Apparatus with a Bio-measurement Instrument" discloses the configuration of attaching a bio-measurement instrument which can measure an electrocardiogram signal, body fat or a pulse waveform by a portable apparatus, thereby enabling a user to obtain his/her bio-health information at any time and at any place. However, since the portable apparatus according to this publication includes a pulse waveform sensor and an electrocardiogram signal sensor fixed to a particular location on the user, the portable apparatus may measure pulse waveforms only from a finger of the user.

Namely, the portable apparatus according to this publication has no option but to measure the pulse only from a finger tip, not a radial pulse which is generally used when measuring a user's pulse. Thus, there is a problem that errors may frequently occur when a biosignal is measured. Also, the portable apparatus according to this publication uses a finger tip pulse measured from a finger of the user without consideration of the correlation between the pulse and electrocardiogram. Thus, there is a disadvantage that a large error may occur in the measuring of the pulse waveform.

FIG. 1, parts (a) and (b), are graphs illustrating an error which may occur when a pulse is measured without consideration of the accompanying electrocardiogram according to the conventional art.

As shown in part (a) of FIG. 1, the pulse may repeat similar waveforms per certain cycle. Namely, in part (a) of FIG. 1, sections 1(110), 2(120), and 3 (130) may each be recognized as a waveform, respectively.

However, it is highly possible that the waveforms may include noise caused by the shaking of the pulse waveform sensor or measuring instrument. Accordingly, when the waveform is recognized only by the pulse waveform, there is a very high possibility of a serious error occurring.

For example, section 2(120) has been recognized as one waveform in part (a) of FIG. 1, however, when the electrocardiogram and pulse waveform are compared as shown in part (b) of FIG. 1, it can be known that the section 2(120) is not one waveform but two waveforms, which are sections 2-1(121) and 2-2(122). Accordingly, when of a measurement of the pulse waveform by itself, an error frequently occurs when the waveform is recognized because of the noise included therein. Due to this, there is a great difficulty in acquiring biosignal information about a user.

Because of the aforementioned problems in the conventional art, there is a demand for the development of a portable device, which can be used at any time and at any place, having a biosignal measuring instrument which enables a user to simultaneously measure his/her pulse and electrocardiogram signals, thereby obtaining more precise biometric information.

BRIEF SUMMARY

An aspect of the present invention provides a portable device having a biosignal measuring instrument which can measure a user's electrocardiogram signal and pulse waveform simultaneously via an electrocardiogram signal sensor and a pulse waveform sensor, detect characteristic points of the pulse waveform by referring to the electrocardiogram waveform, reduce the error of the pulse waveform which may occur due to external noise like the shaking of a hand, and thereby obtain more accurate biosignal information.

An aspect of the present invention also provides a portable device having a biosignal measuring instrument which enables a user to measure his/her biosignal more easily by respectively attaching the electrocardiogram signal sensor and the pulse sensor to the side or the bottom of the portable device or to the tip of the antenna thereof such that the user may measure his/her electrocardiogram signal and pulse waveform unassisted.

An aspect of the present invention also provides a portable device having a biosignal measuring instrument which can obtain a user's pulse waveform via a pulse waveform sensor. This pulse waveform sensor is a transducer which converts the radial arterial pulse waveform sensed from the wrist of the user into an electric signal, thereby measuring the pulse waveform more accurately and effectively when compared to measuring the pulse from a finger.

An aspect of the present invention also provides a portable device having a biosignal measuring instrument which can transmit the pulse waveform of a user measured via an electrocardiogram signal sensor and a pulse waveform sensor, and provide the user with the result of the pulse waveform analysis according to the characteristic points, to a predetermined output means via a short-distance communication module, thereby embodying U-HealthCare.

According to an aspect of the present invention, there is provided a portable device having a biosignal measuring instrument, including: at least one first electrocardiogram signal sensor portion provided on a first surface of the portable device that a user can make contact with while grasping the portable device with his/her first hand, to measure a first electrocardiogram signal of the user; at least one second electrocardiogram signal sensor portion provided on a second surface of the portable device that is in contact with the wrist of a second hand of the user, to measure a second electrocardiogram signal from the wrist; a pulse waveform sensor provided on the second surface parallel to the second electrocardiogram signal sensor portion, to measure the pulse waveform from the wrist; a waveform controller generating an electrocardiogram waveform and a pulse waveform of the user from the measured first and second electrocardiogram signals and from the sensed pulse waveform, respectively, and detecting at least one characteristic point of the pulse waveform by referring to the electrocardiogram waveform; and an output means for providing the result of the pulse waveform analysis of the user based on the detected characteristic point.

According to another aspect of the present invention, there is provided a portable device having a biosignal measuring instrument, including: a first sensor portion which includes a first pulse waveform sensor connected to the portable device via a predetermined terminal which makes contact with the neck of a user, thereby converting the carotid pulse of the user into an electric signal, and a first electrocardiogram signal sensor for detecting a first electrocardiogram signal of the user; a second sensor portion including a second pulse waveform sensor provided on one surface of the portable device to make contact with the wrist of the user, thereby converting the radial arterial pulse of the user into an electric signal, and a second electrocardiogram signal sensor for measuring a second electrocardiogram signal of the user; a waveform controller generating an electrocardiogram waveform and a pulse waveform of the user from the measured first and second electrocardiogram signals and carotid pulse and radial arterial pulse waveforms converted into electric signals, respectively, and detecting at least one characteristic point of the pulse waveform by referring to the electrocardiogram waveform; and an output means for providing the result of the pulse waveform analysis of the user based on the detected characteristic point.

According to still another aspect of the present invention, there is provided a portable biosignal measuring instrument, including: a wrist supporter formed of a band located around the wrist of a first hand of a user; a pulse waveform sensor provided inside the wrist supporter to make contact with the wrist of a first hand, thereby converting the pulse of the user into an electric signal; a first electrocardiogram signal sensor portion provided inside the wrist supporter, to measure a first electrocardiogram signal from the wrist of a first hand; a second electrocardiogram signal sensor portion provided independent from the wrist supporter, to measure a second electrocardiogram signal from a second hand of the user; and a waveform controller generating an electrocardiogram waveform and a pulse waveform of the user from the measured first and second electrocardiogram signals and from the pulse waveform converted electric signals, respectively, and detecting at least one characteristic point of the pulse waveform by referring to the electrocardiogram waveform; and an output controller controlling a predetermined output means for providing the result of pulse wave analysis based on the detected characteristic point to the user, wherein the portable biosignal measuring instrument is formed to be similar in appearance as a wristwatch band.

According to still another aspect of the present invention, there is provided a portable device, including: a first electrocardiogram signal sensor on a first surface of the portable device, in contact with a first hand of a user, and measuring a first electrocardiogram signal of the user; a second electrocardiogram signal sensor on a second surface of the portable device, in contact a wrist of a second hand of the user, and measuring a second electrocardiogram signal of the user; a pulse waveform sensor on the second surface, in parallel with the second electrocardiogram signal sensor portion, and sensing a pulse waveform from the wrist; and a waveform controller generating an electrocardiogram waveform from the measured electrocardiogram signals, generating a pulse waveform from the sensed pulse waveform, and detecting at least one characteristic point of the pulse waveform with reference to the electrocardiogram waveform, the at least one characteristic point being usable in a pulse wave analysis.

Additional and/or other aspects and advantages of the present invention will be set forth in part in the description which follows and, in part, will be obvious from the description, or may be learned by practice of the invention.

BRIEF DESCRIPTION OF THE DRAWINGS

The above and/or other aspects and advantages of the present invention will become apparent and more readily appreciated from the following detailed description, taken in conjunction with the accompanying drawings of which.

DETAILED DESCRIPTION OF EMBODIMENTS

Figure 1:
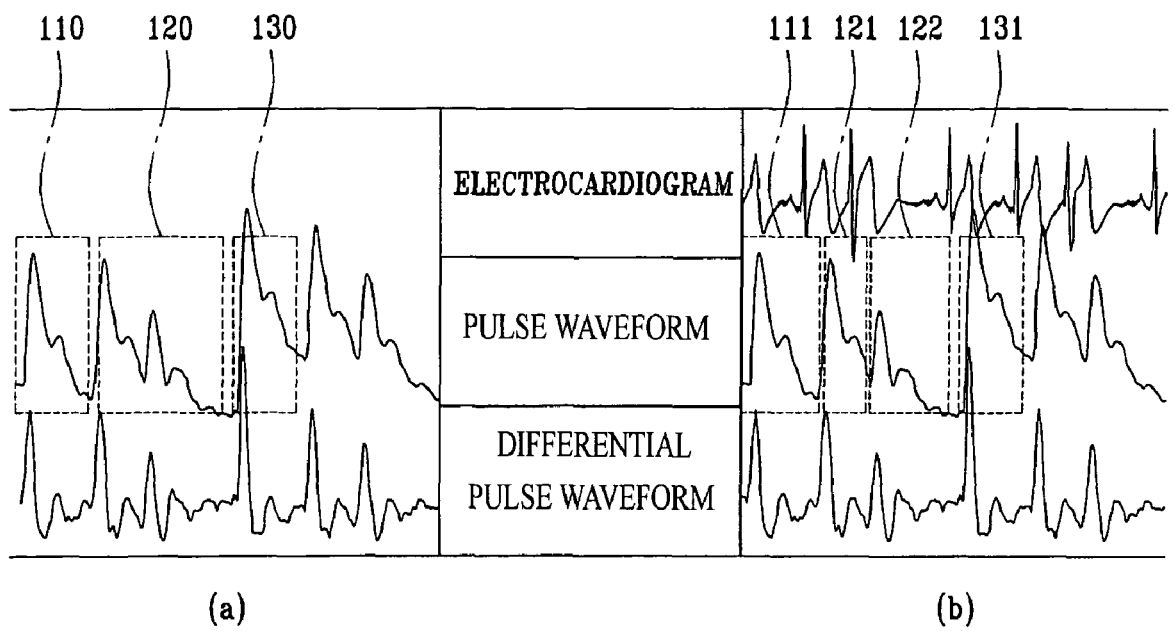
FIG. 1, parts (a) and (b), are graphs illustrating an error which may occur when a pulse wave is measured without reference to an electrocardiogram according to the conventional art.

Reference will now be made in detail to embodiments of the present invention, examples of which are illustrated in the accompanying drawings, wherein like reference numerals refer to the like elements throughout. The embodiments are described below in order to explain the present invention by referring to the figures.

As used in the description that follows, the term "electrocardiogram" (ECG) mainly refers to standards for an electrocardiogram, and may be described as a graph illustrating the electrical activity of a heart which is obtained by inducing an amperemeter (electrocardiograph) at two random points of the human body by the excitation of the myocardium. The excitation of the myocardium rises from sinuses carotid sinus and extends in the direction of atrial rem. What is obtained through the aforementioned method is an electrocardiogram, and the electrocardiogram may be very important data to be used as not only for diagnosing heart disease, but also for diagnosing coronary artery disease such as angina pectoris, a myocardial infraction, or other disorders such as arrhythmia or electrolyte disorder, or for verifying during surgery the patient's heart is not developing any complications.

As a method for measuring the electrocardiogram signal, a portable device having a biosignal measuring instrument according to an embodiment of the present invention may apply a method of measuring an electrocardiogram signal according to standard limb leads, including first induction of an amperemeter from both hands, second induction of an amperemeter from the right hand and the left foot, and third induction of an amperemeter from the left hand and the left foot. Besides the immediately preceding method, the portable device may include and apply not only a method of measuring an electrocardiogram signal according to unipolar induction or chest induction, but also all electrocardiogram signal measuring methods which can be generally implemented.

Also, in the description that follows, the term "a pulse waveform" mainly means a waveform according to the change of the pressure and volume of a blood vascular system and a heart chamber on the basis of a physical change of the heart. The portable device having a biosignal measuring instrument according to an embodiment of the present invention can measure a radial arterial pulse waveform from the wrist of the user and a carotid pulse waveform from the neck of the user, respectively.

Also, in the description that follows, the term "portable device" includes mobile terminals such as a PDA (Personal Digital Assistant), a cellular phone, a PCS (Personal Communication Service) phone, a hand-held PC, a CDMA (Code Division Multiple Access)-2000 (1X, 3X) phone, WCDMA (Wideband CDMA) phone, a Dual Band/Dual Mode phone, a GSM (Global Standard for Mobile) phone, an MBS (Mobile Broadband System) phone, a satellite/ground DMB (Digital Multimedia Broadcasting) phone, etc., and an MP3 player, a portable game, a notebook computer, and the like.

Figure 2:
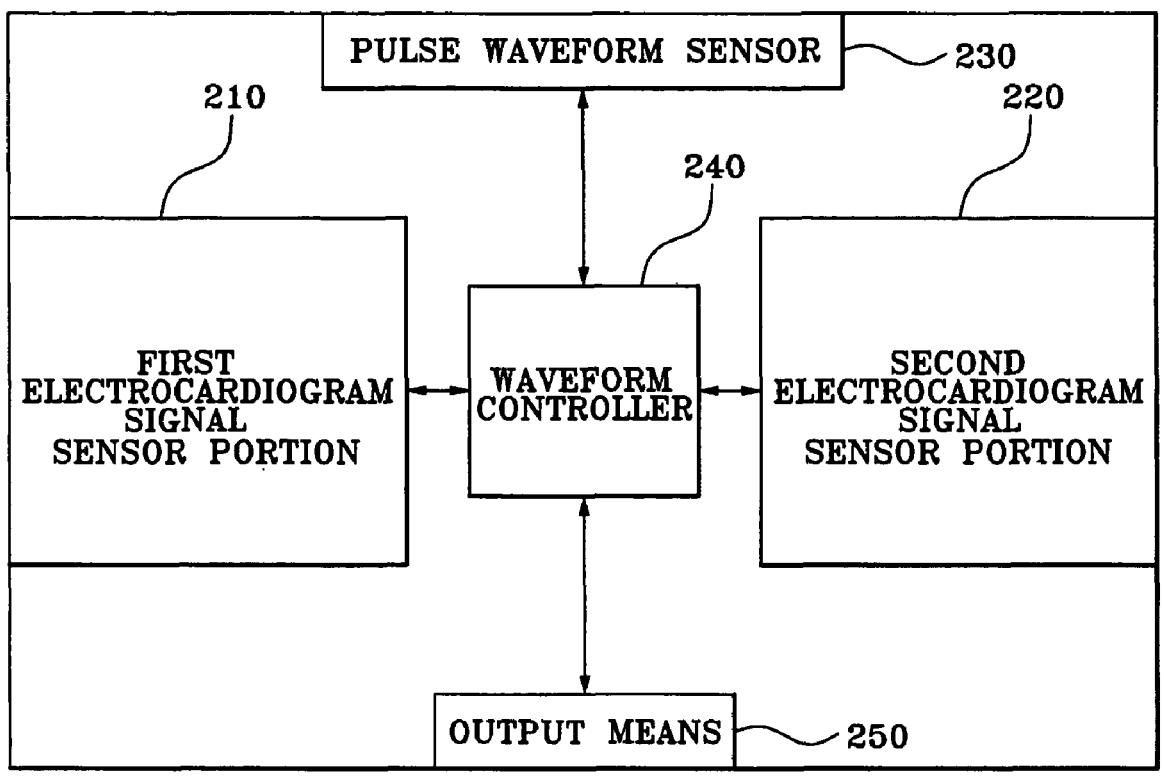
FIG. 2 is a block diagram illustrating a configuration of a biosignal measuring portable device according to a first embodiment of the present invention.

FIG. 2 is a block diagram illustrating a configuration of a biosignal measuring portable device according to a first embodiment of the present invention.

A portable device 200 having a biosignal measuring instrument according to the first embodiment of the present invention includes a first electrocardiogram signal sensor portion 210, a second electrocardiogram signal sensor portion 220, a pulse waveform sensor 230, a waveform controller 240, and an output means 250.

At least one first electrocardiogram signal sensor portion 210 is provided on a first surface of the portable device 200 that a user can make contact with a first hand, and measures a first electrocardiogram signal of the user from a first hand of the user who has grasped the portable device 200. For example, the first electrocardiogram signal sensor that the user makes contact with as the user grasps the portable device 200 may be provided on the side of the portable device 200.

At least one second electrocardiogram signal sensor portion 220 is provided on a second surface of the portable device 200 that is in contact with the wrist of a second hand of the user and measures a second electrocardiogram signal from the wrist. For example, the second electrocardiogram signal sensor may be provided the bottom of the portable device 200 or on the tip of the antenna thereof. In this instance, the second hand is different from the first hand which has grasped the portable device 200.

One or more electrocardiogram signal sensors included in the first electrocardiogram signal sensor portion 210 and the second electrocardiogram signal sensor portion 220 may be electrodes which are used in general electrocardiographs.

The pulse waveform sensor 230 is provided on a second surface of the portable device 200 in parallel with the second electrocardiogram signal sensor portion 220, senses a pulse waveform from the wrist of the second hand of the user, and converts the sensed pulse waveform into an electric signal. For example, the pulse waveform sensor 230 may be provided on the bottom of the portable device 200 or on the tip of the antenna thereof, in parallel with the electrocardiogram signal sensor 220. The pulse sensor 230 may be embodied in a predetermined transducer means which senses and converts a radial arterial pulse waveform from the wrist of the user into an electric signal.

The portable device having the biosignal measuring instrument according to the first embodiment of the present invention includes two examples which differ with respect to the positions on which the first electrocardiogram signal sensor portion 210, the second electrocardiogram signal sensor portion 220, and the pulse waveform sensor 230 are provided respectively. These two examples will be described in detail with reference to FIGS. 3 and 4, respectively.

Figure 3:
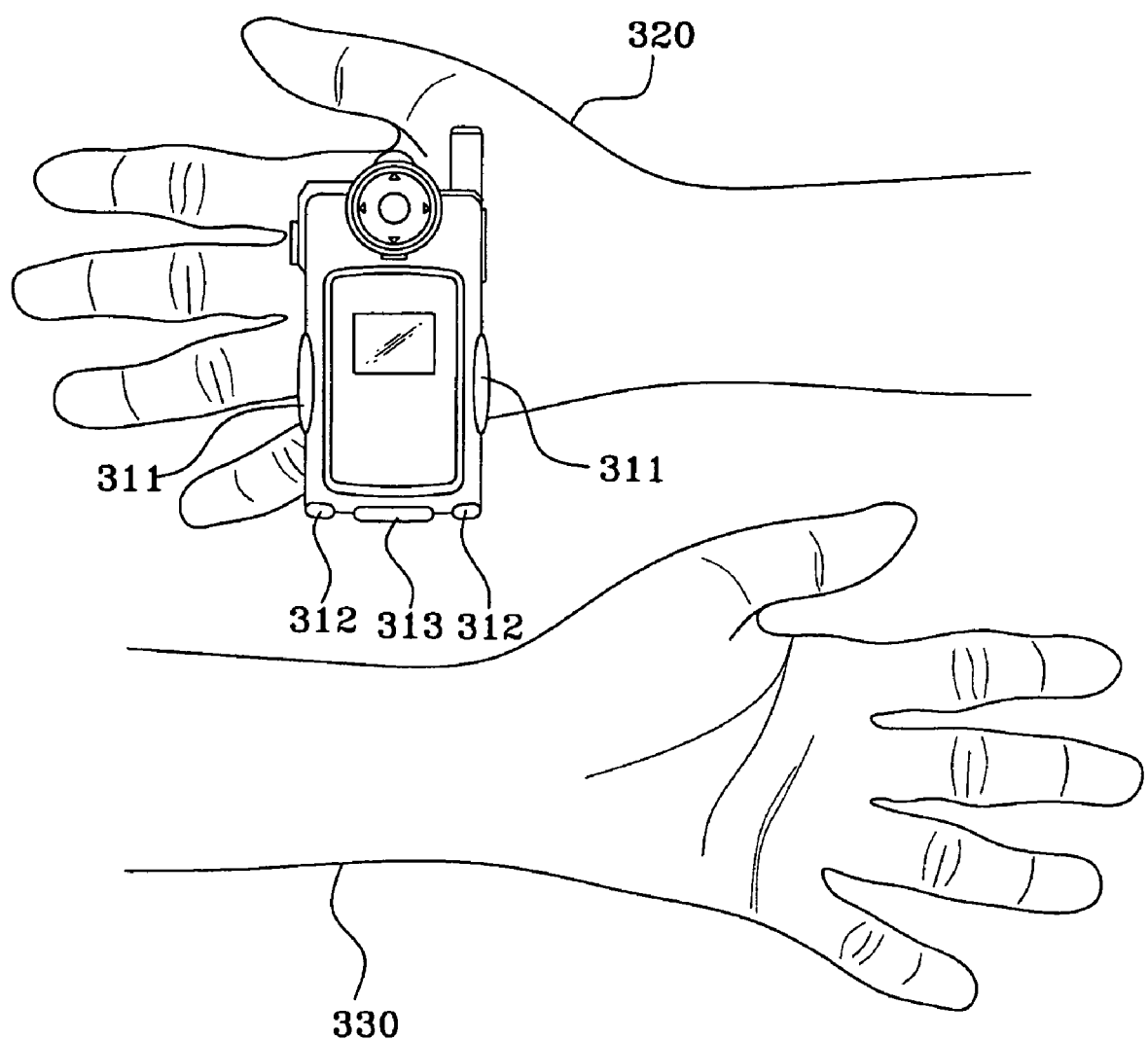
FIG. 3 is a view illustrating the external appearance of a portable device having a biosignal measuring instrument according to Embodiment 1-1 of the present invention.

FIG. 3 is a view illustrating the external appearance of a portable device having a biosignal measuring instrument according to a first example of the present embodiment of the present invention.

As shown in FIG. 3, at least one electrocardiogram signal sensor of a first electrocardiogram signal sensor portion 311 may be provided on the side of a portable device, at least one electrocardiogram signal sensor of a second electrocardiogram signal sensor portion 312 provided on the bottom of the portable device, and a pulse waveform sensor 313 provided on the bottom thereof in parallel with the second electrocardiogram signal sensor portion 312.

A user may measure an electrocardiogram signal and a pulse waveform in this first example according to the present embodiment of the present invention, by grasping the side of the portable device with a first hand 320 and making contact with the bottom of the portable device to the wrist of a second hand 330. For example, the user may make contact with the bottom of the portable device to the wrist of the second hand 330 while grasping the side of the portable device 311 with the first hand 320.

In this instance, the first electrocardiogram signal sensor portion 311 provided on the side of the portable device measures a first electrocardiogram signal from the right hand 320 of the user, and the second electrocardiogram signal sensor portion 312 provided on the bottom measures a second electrocardiogram signal from the wrist of the second hand 330 of the user. In this manner, an electrocardiogram of the user can be measured.

Also, the pulse waveform sensor 313 provided on the bottom of the portable device senses and converts a pulse waveform from the wrist of the left hand 330 of the user into an electric signal. In this manner, the pulse waveform of the user can be measured.

In this first example according to the present embodiment of the present invention as constructed above, the user may measure his/her electrocardiogram signal and pulse waveform with the simple motions of grasping the portable device by a first hand 320 and making contact with the same to the wrist of a second hand 330. Also, since the aforementioned motions facilitate the user to grasp the portable device with one hand and place the same to the wrist of the other hand, shaking of the portable device is prevented. Thus, there is an effect that sensing and measuring the radial arterial pulse waveform can be accomplished with more precision.

Figure 4:
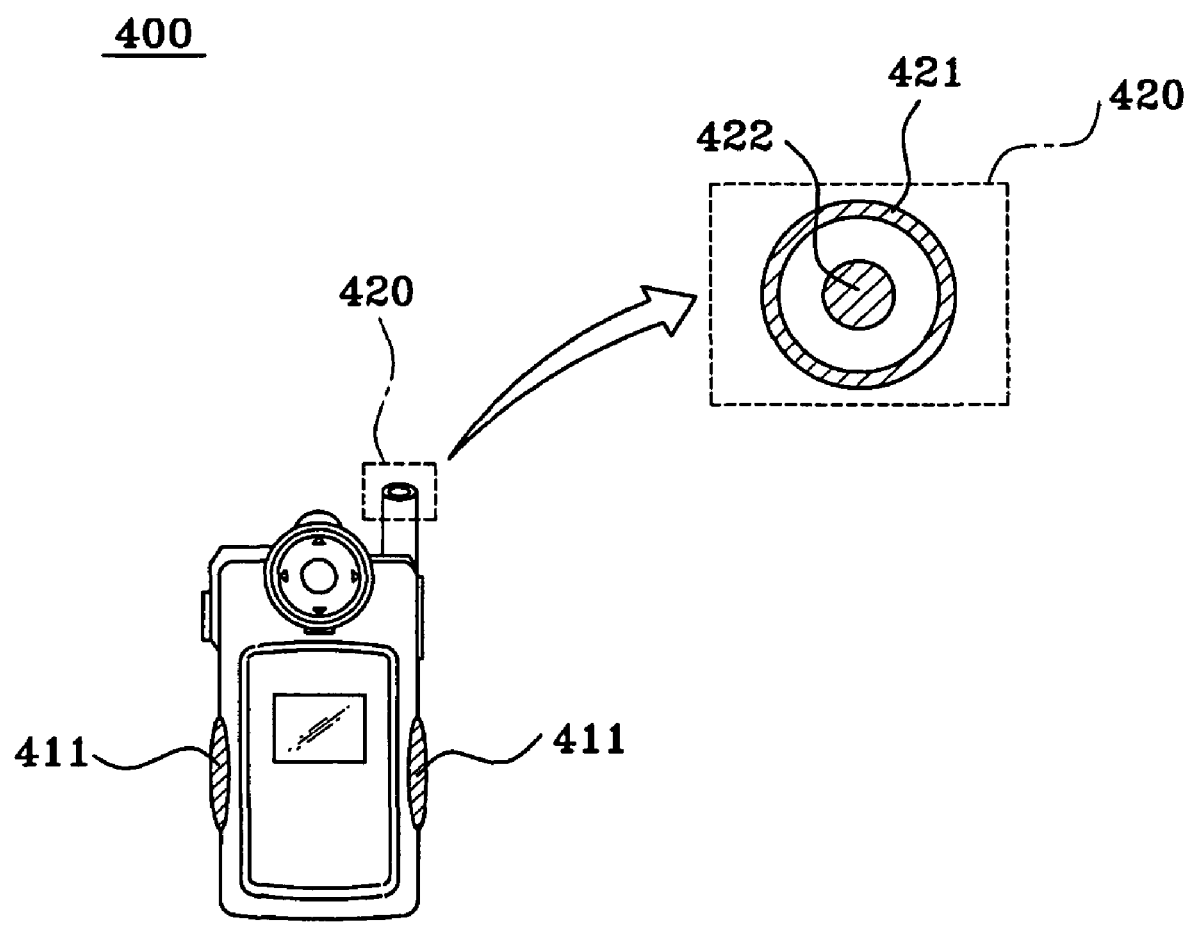
FIG. 4 is a view illustrating the external appearance of a portable device having a biosignal measuring instrument according to Embodiment 1-2 of the present invention.

FIG. 4 is a view illustrating the external appearance of a portable device having a biosignal measuring instrument according to a second example according to the present embodiment of the present invention.

As shown in FIG. 4, at least one electrocardiogram signal sensor of a first electrocardiogram signal sensor portion 411 may be provided on the side of a portable device, and a second electrocardiogram signal sensor portion 421 and a pulse waveform sensor 422 may be provided on the tip of the antenna 420 of the portable device.

The second electrocardiogram signal sensor portion 421 is provided along the circumference of the tip of the antenna 420, and the pulse sensor 422 may be provided at the center of the tip of the antenna 420. This configuration is a result of the characteristic of the pulse waveform sensor 422 that has to sense the pulse waveform from a certain part of the wrist of a user. It is to be understood that the specific sensor illustrated in FIG. 4 is but one non-limiting example and that other arrangements are contemplated. Also, while the tip of the antenna is illustrated as circular, it is to be understood that other configurations are contemplated such as, for example, a polygon.

A user may measure an electrocardiogram signal and a pulse waveform, in accordance with this second example of the present embodiment of the present invention, by grasping the side of the portable device with a first hand and making contact with the bottom of the portable device to the wrist of a second hand.

In this instance, the first electrocardiogram signal sensor portion 411 provided on the side measures a first electrocardiogram signal from the first hand, and the second electrocardiogram signal sensor portion 421 provided on the tip of the antenna 420 measures a second electrocardiogram signal from the wrist of the second hand. In this manner, an electrocardiogram signal of the user can be measured. Also, the pulse sensor 422 provided on the tip of the antenna 420 senses and converts a pulse waveform from the wrist of the second hand into an electric signal. In this manner, the pulse waveform of the user can be measured.

In this second example of the present embodiment of the present invention, since the shaking of the portable device 400 can be prevented to the greatest extent possible, a user can measure his/her electrocardiogram signal and pulse waveform simply and easily by using both hands, and also, can measure a radial arterial pulse waveform which senses and measures the pulse waveform from a radial artery.

Referring again to FIG. 2, the waveform controller 240 generates an electrocardiogram waveform of the user from the measured first electrocardiogram signal and second electrocardiogram signal, generates a pulse waveform of the user from the sensed pulse waveform, and detects at least one characteristic point of the pulse waveform by referring to the electrocardiogram waveform.

Namely, the waveform controller 240 may generate the user's electrocardiogram waveform from the measured first electrocardiogram signal and second electrocardiogram signal via the first electrocardiogram signal sensor portion 210 and the second electrocardiogram signal sensor portion 220, respectively. Also, the waveform controller 240 may generate the user's pulse waveform by using data in which the radial arterial pulse waveform measured via the pulse waveform sensor 230 has been converted into an electric signal. The waveform controller 240 may synchronize the electrocardiogram waveform and the pulse waveform akin to the graph illustrated in part (b) of FIG.1 and display the same on the same graph.

The waveform controller 240 may detect at least one characteristic point of the pulse waveform of the user from the synchronized electrocardiogram waveform and pulse waveform. The characteristic point of the pulse waveform relates to the feature of a pulse waveform which may occur in a particular section in pulse waveforms repeating per certain cycle. This detection will be described in detail with reference to FIG. 5.

Figure 5:
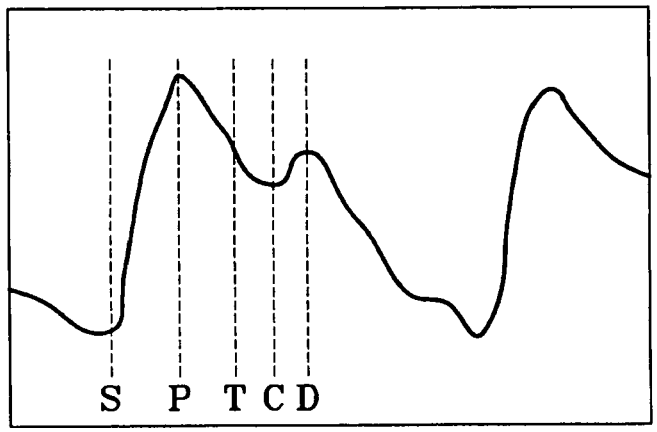
FIG. 5 is a graph illustrating at least one characteristic point of a pulse waveform.

FIG. 5 is a graph illustrating at least one characteristic point of pulse waveforms.

The graph illustrated in FIG. 5 shows a particular cycle section among pulse waveforms repeating per certain cycle. Generally, a pulse waveform has characteristic points such as S, P, T, C, and D for one cycle. Since a pulse waveform is generated by the physical exertion of the heart, the characteristic points have the close relation thereto.

Also, in view of the biological meaning of the pulse waveform related to cardiac contraction, it is known the contraction of the left ventricle of the heart starts at the characteristic point S. It is known the contraction of the left ventricle has been maximized at the characteristic point P, and the aortic wall has inflated after the contraction of the left ventricle and the blood flow has been reduced in the section of the characteristic point T. Also, it is known the blood flow has been further reduced at the characteristic point C, and an elastic wave of the myocardium and membrane generates the characteristic point D.

As above, all sorts of biometric information about a user can be obtained through each characteristic point of the pulse waveform of the user. However, since the pulse waveform is measured by sensing a radial arterial pulse waveform from the wrist of the user, noise due to the external environment such as the shaking of a hand or the like may occur. If noise does occur, it becomes difficult to precisely read each characteristic point from the pulse waveform. Thus, precise biometric information about the user may not be obtained.

Accordingly, the waveform controller 240 of FIG. 2 may detect the characteristic points of a pulse waveform by referring to an electrocardiogram waveform synchronized with the pulse waveform. Since the electrocardiogram waveform is generated by receiving an electric signal from a user via an electrocardiogram signal sensor composed of electrodes, it is not affected by shaking or the like. Accordingly, the waveform controller 240 may more precisely detect characteristic points of the pulse waveform, while ignoring noise such as the shaking of a hand or the like.

The output means 250 of FIG. 2 provides the user with the result of a pulse waveform analysis based on the characteristic points of the pulse waveform which are detected by the waveform controller 240 of FIG. 2. The output means 250 may include a means of recording a predetermined biometric information program so as to output the result of pulse waveform analysis according to the characteristic points.

Also, the output means 250 of FIG. 2 may include any one or more of the following: a speaker means providing the result of pulse waveform analysis by audible data; a vibration means providing the same by vibrating; or a display means visually displaying the same. Namely, the output means 250 may be constructed to include all sorts of output devices included in the portable device 200.

Figure 6:
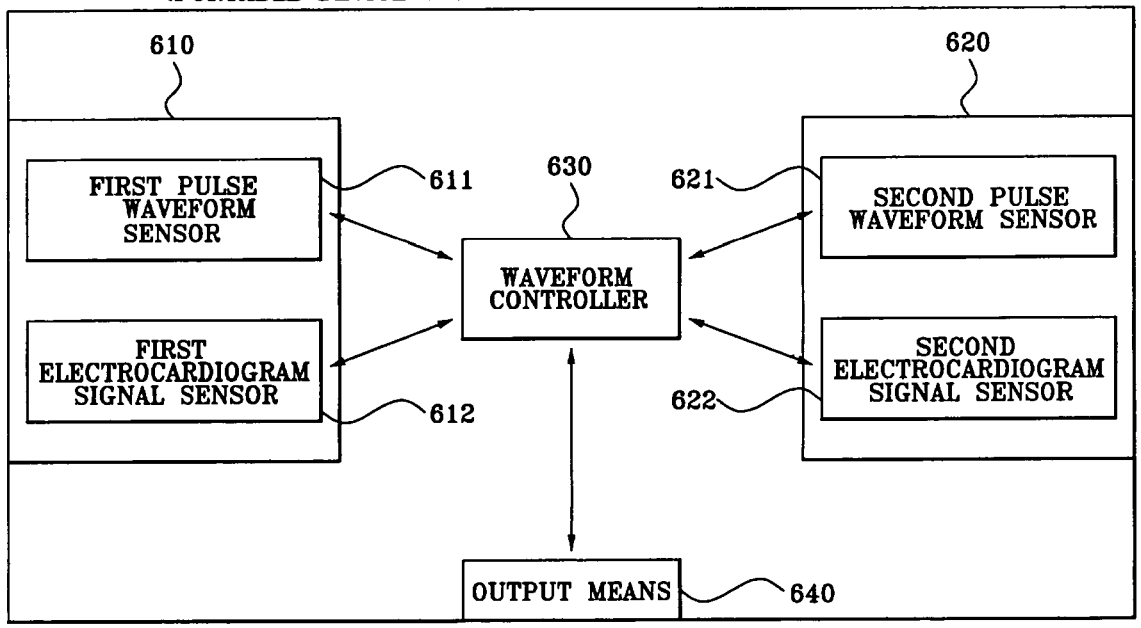
FIG. 6 is a block diagram illustrating a configuration of a portable device having a biosignal measuring instrument according to a second embodiment of the present invention.

FIG. 6 is a block diagram illustrating a configuration of a portable device having a biosignal measuring instrument according to a second embodiment of the present invention.

A portable device 600 having a biosignal measuring instrument according to the second embodiment of the present invention may be used in traditional oriental medicine in taking the negative and positive pulse by measuring a carotid pulse waveform from the neck of a user and measuring a radial arterial pulse waveform from the wrist of the user.

The portable device 600 having the biosignal measuring instrument according to the second embodiment of the present invention includes a first sensor portion 610, a second sensor portion 620, a waveform controller 630, and an output means 640.

The first sensor portion 610 includes a first pulse waveform sensor 611 which is connected to the portable device 600 via a predetermined cable to make contact with the neck of a user, thereby converting a carotid pulse waveform of the user into an electric signal, and a first electrocardiogram signal sensor 612 for measuring a first electrocardiogram signal of the user.

The first sensor portion 610 may be constructed to be removably attached to the portable device 600 via the cable. The cable is constructed to include a predetermined elastic acoustic device, which makes it easier for the user to removably attach the first sensor portion 610 to the portable device 600.

The second sensor portion 620 includes a second pulse waveform sensor 621 provided on one surface of the portable device 600 to make contact with the wrist of the user, thereby converting a radial arterial pulse waveform of the user into an electric signal, and a second electrocardiogram signal sensor 622 for measuring a second electrocardiogram signal of the user The second sensor portion 620 may be fixed on one surface of the portable device 600. For example, the second sensor portion 620 may be provided to be fixed on the bottom, side, or tip of the antenna of the portable device 600, as in the first embodiment of the present invention.

Also, the second sensor portion 620 may be provided in the same form as the first sensor portion 610. Namely, the second sensor portion 620 may be constructed to be removably attached to the portable device 600 via a second cable which is identical to the first cable.

A configuration of connecting the first sensor portion 610 and the second sensor portion 620 to the portable device 600 via a cable as above will be described in detail with reference to FIG. 7.

Figure 7:
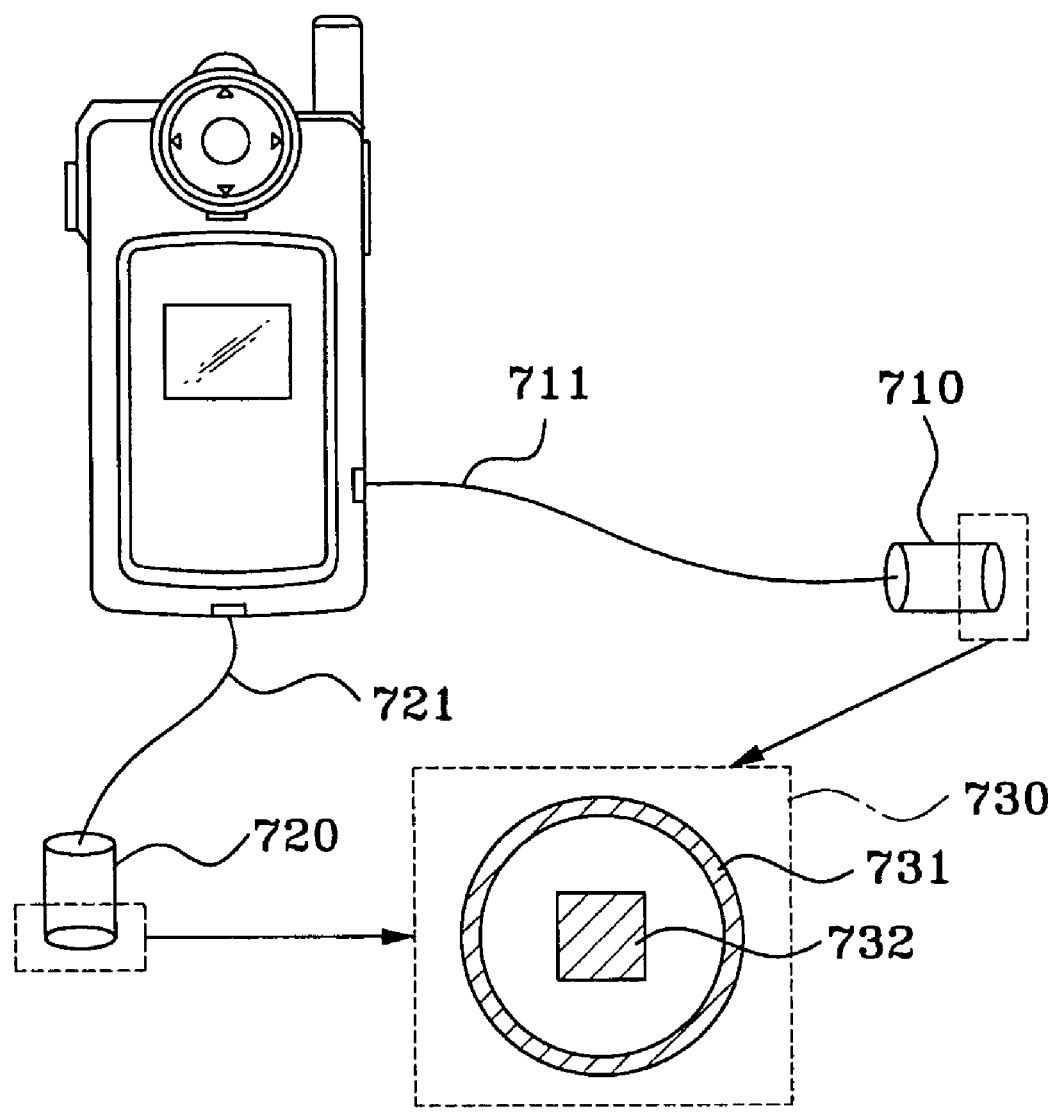
FIG. 7 is a view illustrating the external appearance of a portable device having a biosignal measuring instrument according to a second embodiment of the present invention.

FIG. 7 is a view illustrating the external appearance of the portable device having the biosignal measuring instrument according to the second embodiment of the present invention.

Referring to FIG. 7, a portable device according to the second embodiment of the present invention includes a first sensor portion 710 connected via a first cable 711 and a second sensor portion 720 via a second cable 721. The first sensor portion 710 and the second sensor portion 720 may be removably attached to the portable device 700 via the first cable 711 and the second cable 721 respectively, thereby making contact with the neck or hand of a user.

The first sensor portion 710 and the second sensor portion 720 may be formed of a cylinder, as illustrated in FIG. 7, or a prism. In this case, an electrocardiogram signal sensor and a pulse waveform sensor may be provided to the base side 730 of the cylinder or prism.

Namely, an electrocardiogram signal sensor 731 may be provided along the circumference of the base side of the cylinder 730, and a pulse waveform sensor 732 may be provided at the center of the base side of the cylinder 730. This is a result of the characteristic of the pulse waveform sensor 732 that has to sense the pulse waveform from a certain part of the wrist of a user. Thus, various methods are applicable in accordance with the decision of those skilled in the related art, besides the structure of the sensor illustrated in FIG. 7. The electrocardiogram signal sensor 731 may be embodied in an electrode included in a general electrocardiogram signal measuring instrument, and the pulse sensor 732 may be embodied in a predetermined transducer converting a pulse waveform into an electric signal.

A user may make contact with the first sensor portion 710 to his/her neck and the second sensor portion 720 to his/her wrist in order to measure the negative and positive pulse according to the second embodiment of the present invention. In this instance, the portable device may sense a carotid pulse waveform of the user from a first pulse waveform sensor of the first sensor portion 710 making contact with the neck of the user and convert the same into an electric signal. Also, the portable device may sense a radial arterial pulse waveform of the user from a second pulse waveform sensor of the second sensor portion 720 making contact with the wrist of the user and convert the same into an electric signal.

Also, the portable device may measure a first electrocardiogram signal of the user from a first electrocardiogram signal sensor of the first sensor portion 710 making contact with the neck of the user, and measure a second electrocardiogram signal of the user from a second electrocardiogram signal sensor of the second sensor portion 720 making contact with the wrist of the user.

Referring again to FIG. 6, the waveform controller 630 generates an electrocardiogram waveform of the user from the measured first electrocardiogram signal and second electrocardiogram signal. Also, the waveform controller 630 generates a pulse waveform of the user from the electric signals that were converted from the carotid pulse wave and the radial arterial pulse waveform. Namely, the portable device 600 according to the second embodiment of the present invention may generate a pulse waveform via measurement of the negative and positive pulse by using the electric signals converted from the carotid pulse waveform and the radial arterial pulse waveform respectively, measured from the neck and the wrist of the user.

The waveform controller 630 detects at least one characteristic point of the pulse waveform by referring to the generated electrocardiogram waveform. How to detect the characteristic point may be embodied in an identical method to the method of detecting characteristic points of the portable device 200 having the biosignal measuring instrument according to the first embodiment of the present invention, which has been described through FIGS. 2 to 5. Thus, a detailed description related thereto will be omitted.

The output means 640 provides the user with the result of the pulse waveform analysis according to the characteristic point of the pulse waveform detected by the waveform controller 630. The output means 640 may include a means of recording a predetermined biometric information program in order to calculate the result of the pulse waveform analysis according to the characteristic point.

Also, the output means 640 may include any one or more of the following: a speaker means providing the result of pulse waveform analysis by audible data; a vibration means providing the same by vibrating; or a display means visually displaying the same. Namely, the output means 640 may be constructed to include all sorts of output devices included in the portable device 600.

According to the portable devices 600 and 700 having the biosignal measuring instrument according to the second embodiment of the present invention, which has been described with reference to FIGS. 6 and 7, more precise biosignal information can be obtained in such a manner that the waveform controller 630 detects a characteristic point of the pulse waveform by referring to the electrocardiogram waveform synchronized with the pulse waveform. Also, the negative and positive pulse can be effectively measured by generating a pulse waveform from a carotid pulse wave measured from the neck of a user and a radial arterial pulse wave measured from the wrist of the user.

In a portable device having a biosignal measuring instrument as described above, the biosignal measuring instrument may be constructed to be integrated into the portable device. Also, the biosignal measuring instrument may be constructed to be detachable, i.e. not integrated. The biosignal measuring instrument constructed to be integrated into the portable device will be described in detail with reference to parts (a) and (b) of FIG. 8.

Figure 8:
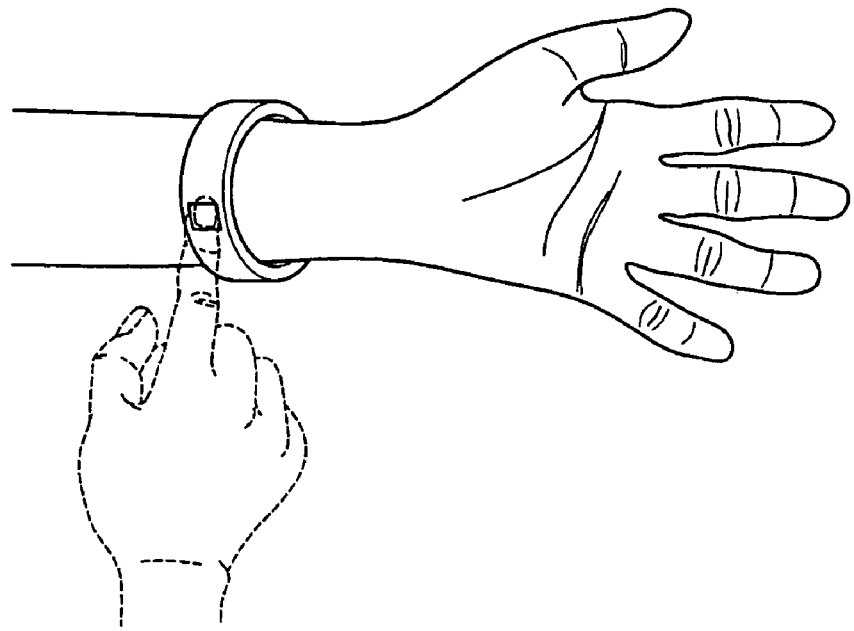
FIG. 8, parts (a) and (b), are views illustrating a configuration of a portable biosignal measuring instrument according to another embodiment of the present invention.
Figure 8:
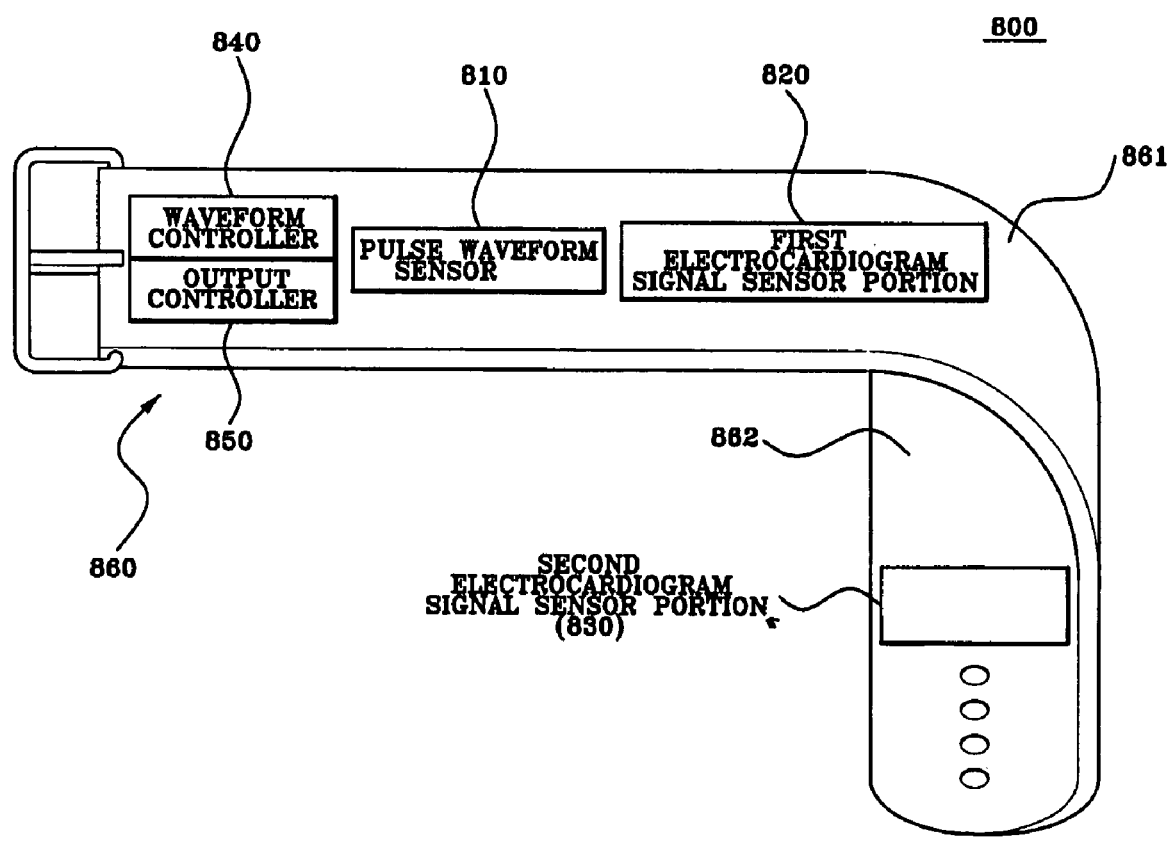

FIG. 8, parts (a) and (b), are views illustrating a configuration of a portable biosignal measuring instrument according to another embodiment of the present invention.

According to another embodiment of the present invention, a portable biosignal measuring instrument 800 may be formed to have an appearance similar to the band of a wristwatch as illustrated in parts (a) and (b) of FIG. 8. The portable biosignal measuring instrument 800 includes a wrist supporter 860, a pulse waveform sensor portion 810, a first electrocardiogram signal sensor portion 820, a second electrocardiogram signal sensor portion 830, a waveform controller 840, and an output controller 850.

The wrist supporter 860 may be formed of a band which is fastened around the wrist of a user. The wrist supporter 860 may be constructed to be a general wristwatch band comprising an inner surface 861 and an outer surface 862.

The pulse wave sensor 810 is provided on the inner surface 861 of the wrist supporter 860 to make contact with the wrist of a first hand of the user, thereby converting a pulse waveform of the user into an electric signal. The pulse waveform sensor may be constructed to be a transducer which senses the oscillation of a radial arterial pulse waveform from the wrist of the user and converts the same into an electric signal.

The first electrocardiogram signal sensor portion 820 is provided on the inner surface 861 of the wrist supporter 860, and measures a first electrocardiogram signal from the first hand of the user. Namely, the first electrocardiogram sensor portion 820 may be provided on the inner surface 861 of the wrist supporter 860 making contact with the wrist of the user and in parallel with the pulse waveform sensor 810.

The second electrocardiogram signal sensor portion 830 is provided on the outer surface 862 of the wrist supporter 860, and measures a second electrocardiogram signal from a second hand of the user. As illustrated in part (a) of FIG. 8, the second electrocardiogram signal sensor portion 830 is provided on the outer surface 862 of the wrist supporter 860. Thus, if the user wears the wrist supporter 860 around the wrist of a first hand, the second electrocardiogram signal sensor portion 830 may be exposed to the outside environment. At this time, the user may measure a second electrocardiogram signal by making contact with his/her second hand to the second electrocardiogram signal sensor portion 830.

The waveform controller 840 records an electrocardiogram waveform of the user from the measured first electrocardiogram signal and second electrocardiogram signal, and generates a pulse waveform of the user from the electric signal converted from the pulse waveform. The waveform controller 840 detects at least one characteristic point of the pulse waveform by referring to the electrocardiogram waveform. How to detect the characteristic point may be embodied in an identical method to the method of detecting a characteristic point of the portable device 200 in FIG. 2 having the biosignal measuring instrument according to the e first embodiment of the present invention, which has been described through FIGS. 2 to 5. Thus, detailed-description related thereto will be omitted.

The output controller 850 controls a predetermined output means for providing the user with the result of pulse waveform analysis according to the detected characteristic point. The output means may be positioned externally from the portable biosignal measuring instrument 800, and may include any one or more of the following: a speaker means providing the result of pulse wave analysis by audible data; a vibration means providing the same by vibrating; and a display means visually displaying the same.

The output controller 850 may further include a short-distance communication module, such that the output means operates to provide a user with the result of the pulse waveform analysis. The output controller 850 transmits the detected characteristic point to the output means via the short-distance communication module, and the output means provides the user with a result of the pulse waveform analysis according to the characteristic point.

The short-distance communication module may include a communication module for performing short-distance communication such as WLAN (Wireless LAN), Bluetooth, UWB (Ultra Wide Band), IrDA (Infrared Data Association), HPNA (Home Phoneline Networking Alliance), SWAP (Shared Wireless Access Protocol), IEEE1394 (FireWire/i.Link), and the like.

The portable biosignal measuring instrument according to another embodiment of the present invention described with reference to parts (a) and (b) of FIG. 8 is one that a user can conveniently carry as if wearing a watch and obtain biosignal information according to the measurement of an electrocardiogram signal and a pulse waveform at any time and at any place. Thus, it is preferably applicable to U-HealthCare. Also, there is an effect that it is possible to ask for outside help more quickly in an emergency situation by transmitting the biometric information to an external terminal or server via the short-distance communication terminal.

A portable device having a biosignal measuring instrument according to the above-described embodiments of the present invention, it is possible to measure a user's electrocardiogram waveform and pulse waveform simultaneously via an electrocardiogram signal sensor and a pulse waveform sensor, detect characteristic points of the pulse waveform by referring to the electrocardiogram waveform, reduce the error of the pulse waveform which may be due to external noise like the shaking of a hand, and thereby obtain biosignal information having improved accuracy.

Also, a portable device having a biosignal measuring instrument according to the above-described embodiments of the present invention, it is possible for user to measure his/her biosignal more easily by respectively attaching the electrocardiogram signal sensor and the pulse waveform sensor to the side or the bottom of the portable device or to the tip of the antenna thereof such that the user may measure his/her electrocardiogram signal and pulse waveform by himself/herself.

Also, a portable device having a biosignal measuring instrument according to the above-described embodiments of the present invention, it is possible to measure a pulse waveform more accurately and effectively by obtaining a user's pulse waveform via a pulse waveform sensor, this is, utilizing a transducer means for converting a radial arterial pulse waveform sensed from the wrist of the user into an electric signal.

Also, a portable device having a biosignal measuring instrument according to the above-described embodiments of the present invention, it is possible to transmit characteristic points of a pulse waveform of a user measured via an electrocardiogram signal sensor and a pulse waveform sensor to a predetermined output means via a short-distance communication module and provide the user with the result of pulse waveform analysis according to the characteristic points via the output means, thereby embodying U-HealthCare.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

What is claimed is:

1. A portable device having a biosignal measuring instrument, comprising:
   a first sensor portion including a first pulse waveform sensor connected to the portable device via a predetermined terminal configured to make contact with a neck of a user, thereby converting a carotid pulse waveform of the user into an electric signal, and a first electrocardiogram signal sensor detecting a first electrocardiogram signal of the user;
   a second sensor portion including a second pulse waveform sensor on a surface of the portable device configured to make contact with a wrist of the user, thereby converting a radial arterial pulse waveform of the user into an electric signal, and a second electrocardiogram signal sensor measuring a second electrocardiogram signal of the user;
   a waveform controller generating an electrocardiogram waveform of the user from the measured first electrocardiogram signal and second electrocardiogram signal, generating a pulse waveform of the user from the electric signals of the converted carotid pulse waveform and radial arterial pulse waveform, and detecting at least one characteristic point of the pulse waveform by referring to the electrocardiogram waveform; and
   an output portion providing a result of the pulse waveform analysis based on the at least one detected characteristic point of the pulse waveform to the user.

2. The portable device of claim 1, wherein the second sensor portion is connected to the portable device via a cable.

3. The portable device of claim 1, wherein the first sensor portion and the second sensor portion are formed as a cylinder or a prism, the first electrocardiogram signal sensor and the second electrocardiogram signal sensor are provided along a circumference of a base side of the cylinder or prism, and the first pulse sensor and the second pulse sensor are provided at a center of a bottom thereof.

4. The portable device of claim 1, wherein the output portion is at least one of: a speaker providing the result of the pulse waveform analysis by audible data; a vibration portion providing the result of the pulse waveform analysis by vibrating; and a display displaying the result of the pulse waveform analysis.

* * * * *